United States Patent [19]

Stapleton

[11] Patent Number: 5,382,511
[45] Date of Patent: Jan. 17, 1995

[54] METHOD FOR STUDYING NUCLEIC ACIDS WITHIN IMMOBILIZED SPECIMENS

[75] Inventor: Marilyn J. Stapleton, Durham, N.C.

[73] Assignee: Gene Tec Corporation, Durham, N.C.

[21] Appl. No.: 935,637

[22] Filed: Aug. 24, 1992

Related U.S. Application Data

[63] Continuation of Ser. No. 227,348, Aug. 2, 1988, abandoned.

[51] Int. Cl.⁶ .......................... C12Q 1/68; C12P 19/34
[52] U.S. Cl. ........................ 435/6; 435/91.1; 435/91.2; 435/287; 435/291; 435/5; 436/501; 536/22.1; 935/77; 935/78; 935/88
[58] Field of Search .......... 435/6, 7.1, 91, 7.2, 435/810, 287, 91.1, 291, 91.2, 5; 436/501, 810; 536/22.1–24.1; 935/78, 88

[56] References Cited

U.S. PATENT DOCUMENTS

| | | | |
|---|---|---|---|
| 4,683,195 | 7/1987 | Mullis et al. | 435/6 |
| 4,683,202 | 7/1987 | Mullis | 435/91 |
| 4,695,548 | 9/1987 | Cantor | 435/179 |
| 5,021,335 | 6/1991 | Tecott et al. | 435/6 |

FOREIGN PATENT DOCUMENTS 0246864 11/1987 European Pat. Off.

OTHER PUBLICATIONS

Takahashi et al., (1984) The Journal of Biological Chemistry, vol. 259, No. 16, pp. 10041–10047.
Wilson et al. (1979) J. Mol. Biol., vol. 132, p. 471.
Murray et al. (1979) J. Mol. Biol, vol. 132 p. 493.
Kinykofer et al. (1983) Electrophoresis, vol. 4, pp. 408–416.
LKB Instruction Manual (1982) *Vertical Electrophoresis* pp. 37–39.
Maniatis et al. (1982) *Molecular Cloning, A Laboratory Manual* (Cold Spring Harbor, N.Y.) pp. 18.47–18.48.
Righetti et al. (1981) J. Biochem. Biophys. Meth, vol. 4, pp. 347–363.
Allen et al. (1986) Acta Histochem Cytochem vol. 19, pp. 637–638.
Nuovo et al. (1991) Am J. of Path., vol. 139, No. 6, pp. 1239–1244.
Barany (1991) Proc. Natl Acad Sci (USA) vol. 88, p. 189.
Bode (1977) Anal. Bioch. vol. 83, p. 204.
Wu et al. (1989) Genomics, vol. 4, pp. 560–569.
Borst et al. (1987) J. of Cellular Biochemistry, vol. 34, pp. 247–258.
Shibata et al. (1988) J. Exp. Med., vol. 167, pp. 225–230.
Saiki et al. (1988) Science, vol. 239, pp. 487–491.
Marx (1988) Science, vol. 240, pp. 1408–1410.
Ou et al. (1988) Science, vol. 239, pp. 295–297.

*Primary Examiner*—Margaret Parr
*Assistant Examiner*—Ardin H. Marschel
*Attorney, Agent, or Firm*—Olive & Olive

[57] ABSTRACT

An apparatus for the automated detection of target nucleic acid sequences in which multiple biological samples are individually incorporated into a matrix and treated in a stepwise fashion to expose, amplify, detect and enumerate the presence of original, target nucleotide sequences in each sample. The samples are held together with other samples in a chamber connected by means of a fluid flow conduit to which the matrices make connection via numerous jet-spray ports for the injection of various fluids from a plurality of reservoirs used to process the samples. Solvents and reagents are used to degrade and wash cellular structures and contaminants away from the nucleic acids. Primer and polymerase molecules are used to replicate the target sequences of nucleic acids in the sample. Labeled DNA probe molecules serve to hybridize to the amplified target sequences for detection. Appropriate buffers allow these manipulations on the nucleic acid molecules in the samples. The system also includes a pump to draw the fluids from the reservoirs and force them through the jet spray manifolds into the main chamber and valves under the control of a microprocessor. The system also includes fans and heating elements for regulating temperature and humidity. Different nucleic acid targets in different biological specimens are accommodated by regulating the quantity, duration, pH, temperature and pressure of fluids flowing from the reservoirs.

16 Claims, 4 Drawing Sheets

METHOD FOR STUDYING NUCLEIC ACIDS WITHIN IMMOBILIZED SPECIMENS

CROSS REFERENCE TO RELATED APPLICATIONS

This patent application is a continuation of copending U.S. patent application Ser. No. 07/227,348 filed Aug. 2, 1988 now abandoned.

BACKGROUND OF THE INVENTION

1. Field of the Invention

This invention relates to a method and apparatus for automating the detection of target nucleic acid sequences in biological-containing samples involving a sequence of physical and chemical reactions, and more particularly to a system for the exposure of, amplification of, and labelled-probe coupling to, a specific, known nucleic acid sequence. The invention is especially suited to the automated detection of single, specific genetic sequences present at random in multiple samples containing biological material without labor-intensive DNA extraction and purification procedures being performed separately on each sample.

2. Description of the Related Art

Instruments for synthesizing polynucleotides have made genetic probes available on a commercial basis. There are now four or more companies selling DNA synthesizers. Improved and more widely known DNA sequencing strategies have enabled researchers to contribute sequence information to the literature and gene databases. The sequence knowledge and the ability to synthesize polynucleotides of a specific sequence have led to the development of genetic probe diagnostics. Wherever a unique, organism-specific polynucleotide sequence is identified, it is possible to use a labeled, synthetic molecule of the unique sequence to determine the presence of the organism by hybridization of the unknown sample to the labeled sequence. This detection method involves hybridization between DNA:RNA hybrids or DNA:DNA duplexes. The probe is a single-stranded nucleic acid molecule complementary to a unique nucleic acid sequence of the gene being tracked. The probe is labeled with an identifying molecule and introduced to the test sample. Hybridization has been an important research tool, but its use is limited to a few clinical laboratories because of the time, skill and knowledge required of the technician performing the test. DNA probes are being used as commercial diagnostics for a few infectious or genetic diseases, but their individual cost is prohibitive for mass screening.

While the common laboratory procedure for hybridization binds the target DNA to a solid support, an alternative approach is solution hybridization or hybridization which requires individual column separation of the unbound, labeled probe for each sample. This invention uses a gel matrix as a solid support. It is not necessary to transfer DNA to a membrane filter after purification and amplification. This approach eliminates any loss of DNA that occurs during transfer. (Purrello and Balazs, 1983, Anal. Biochem. 128:393-397). This paper and all other papers and patents cited herein are hereby incorporated in full by reference.

Presently DNA preparation and amplification require labor-intensive protocols just as hybridization methods do. The only apparatus which automates DNA preparation is the Applied Biosystems Nucleic Acid Extractor, which will process sixteen tissue samples simultaneously in four hours. The sample must comprise homogenous tissue and already contain enough copies of the target DNA to be detected, i.e. about a million copies. The laboratory technician must then either fractionate the extracted DNA by gel electrophoresis or transfer the DNA to a solid support for detection by hybridization to a labeled probe. There is no laboratory apparatus or equipment currently on the market that automates hybridization so that it may be left unattended.

Suspending cells in agarose beads or cubes is a common laboratory procedure for preparing unsheared nucleic acid molecules for subsequent enzymatic modifications. (P. R. Cook, 1984, EMBO 3:1837-1842 and L. Van der Ploeg et al. 1984. Cell: 37:77-84). After solidification the agarose beads or cubes are subjected to extensive treatment with detergent, protease and salt. It is possible to remove all cellular constituents except DNA because the pores in the agarose matrix are large enough to allow rapid diffusion of proteins and other small macromolecules while quantitatively retaining genomic DNA (Smith and Cantor, 1986, Cold Spring Harbor Symposium on Quantitative Biology 51:115-122).

FMC Bioproducts, Rockland, ME, has a nonradioactive-label for DNA in which their product information states that the labeling is done directly in diluted, remelted agarose. This protocol allows electrophoretic fractionation of DNA in agarose and then quick and easy preparation of specific probes (Resolutions 1987 Newsletter 3(2):1-2). FMC also markets a new grade of agarose certified for reliable restriction endonuclease activity. Many other examples exist where research scientists are performing enzymatic modifications on DNA in agarose. D. Persons and O. Finn, (Biotechniques, 1986, 4:398-403) reported primer extension of cDNA on a poly A+ RNA template using a reverse transcriptase in remelted agarose. The method and device of this invention also involves primer extension with polymerase enzymes in agarose.

The above applications using agarose demonstrate its unique properties for DNA manipulations. Agarose is the least charged subcomponent of agar, a mixture of polysaccharides from red algae. It is usually the gel of choice for electrophoresis of particles larger than 5-10 nm in radius. Since agarose is an alternating copolymer with variable amounts of several groups modifying the basic repeating structure, one theory suggests that double helices form during agarose gelation and the double helices cross-link and aggregate to form suprafibres. (P. Serwer, 1983, Electrophoresis 4:375-382). An agarose gel is more rigid than a polyacrylamide gel of the same concentration and an agarose gel has pores larger than the pores of all but the most cross-linked polyacrylamide gel.

Another difficulty that some scientists are trying to address is how to extract DNA from various mixtures in which organisms exist and in which they need to be detected. Human tissue, food products, environmental sources of water, sludge, or soil are among the diverse mixtures in which monitoring of genetic, identifying codes is desirable. If the samples, regardless of origin, could be treated by a standard process in a common apparatus without interference with the nucleic acid identification, then the need for prior nucleic acid extraction and purification steps for identification by hybridization protocols in current laboratory use would be eliminated.

Current practice for nucleic acid identification is done by dot blotting, colony hybridization, Southern transfer or "in situ" either in agarose or in tissue sections with microscopic identification of signal. Most of the hybridizations are performed for research purposes, and some are performed for diagnostic purposes. To recover a genetically altered cell or microbial strain it has been necessary to grow the cell or strain selectively. Direct gene-tracking eliminates the growth component requirement needed when enumerating counts. The processing of DNA or RNA in a solid matrix allows sample preparation, and target DNA amplification and identification of specific sequences without manual transfer of the sample during sequential treatments. The automation of sample-processing will bring accelerated growth to gene-monitoring of microbial, environmental, plant and animal samples.

Immunodiagnostics are commonly used to identify organisms directly by antigenic determinants or to identify individuals by their antibodies which are produced by exposure to the antigen. The same problem is encountered with antigen identification as with DNA probes, i.e. the organism must be cultured if it is not present in sufficient numbers for detection. There is no in vitro method to amplify antibody-binding antigens accurately like there is with primer extension gene amplification. Low population targets in a mixed background cannot be identified immunologically. The gene amplification in vitro has given DNA probes the potential to outperform immunological detection. The accuracy, sensitivity and quantitation potential of DNA probes will make them the diagnostic of choice.

An automated system for simultaneously detecting target nucleic acid sequences from multiple samples must accommodate several different steps and varying reaction conditions. It must be constructed to change reagents and solvents automatically for each stage and monitor time, temperature and pH. If tests are automated and the same apparatus that performs one test for multiple samples in one run could be used for many different tests by changing a few selected reagents, the cost of gene detection would be relatively inexpensive and the system would supersede other methods because of its speed and preciseness.

In order to have enough gene copies for detection, present methods rely on selective cultivation of the organism which takes days to weeks depending upon the organism. A selective DNA amplification technique has been practiced whereby synthetic primers are annealed to single stranded or denatured, double-stranded nucleic acid target sequences and polymerase molecules incorporate nucleotides that replicate a portion of the nucleic acid extending from the primers. Using excess primers in pairs bordering a target sequence in a way that each polymerase extension includes sequences that are complementary to the other primer sequence is a method now termed polymerase chain reaction (PCR) (see U.S. Pat. Nos. 4,683,195 and 4,683,202). This method continues in repetitive rounds of replication until the target sequence has been amplified by a factor of more that 10 million. Saiki et al. reported that a thermostable DNA polymerase improves the specificity, yield, sensitivity and length of products that can be amplified (Saiki, R. K., D. H. Gelfand, S. Stoffel, S. J. Scharf, R. Higuchi, G. T. Horn, K. B. Mullins, and H. A. Ehrlich, Science, 1988, 239:487–491).

A selective gene amplification protocol that can duplicate a single copy of a nucleic acid target in vitro to a sufficient number of copies that can be detected over non-specific background binding with a labeled hybridization probe is the level of sensitivity that will enable easy screening of multiple samples. The accuracy of a gene detection is assured by labeling a probe complementary to a polynucleotide sequence between the two primer sequences for the purpose of hybridization identification. Thus, even if the primers had amplified non-target sequences because of duplicity of sequence or mismatch, the label would only be detected that bound to the target sequence.

The ability to amplify a single target DNA and/or RNA sequence enough to detect it without the cultivation of cells or organisms will simplify gene detection and attempts to automate it. Saiki et al. reported that PCR detects a single copy of target DNA present in one in 1.5 million cells. There is no reason to doubt that gene amplification by primer extension will detect a target DNA segment present at one copy per organism in the starting material. The ability to then quantify how many original copies or organisms there were per sample before amplification will make mass sampling and fate-monitoring possible by hybridization detection. Quantifying methods depend upon diluting the amplified gene so that individual signals are enumerated or intensity of total signal matches that of a known standard concentration.

Using the aforementioned gene amplification protocol, the presence of HIV-1 in peripheral blood mononuclear cells (PBMC) was determined by in situ hybridization to DNA from the PBMC's without prior cultivation of them (Ou, C., S. Kwok, S. Mitchell, D. Mack, J. Sninsky, J. Krebs, P. Feorino, D. Warfield, and G. Schochetman, Science, 1988, 239:295–297). This direct detection method reduces the time to three days from the three to four weeks required for cell cultivation and virus isolation. The polymerase chain extension technique started with DNA isolated from PBMC's, repetitively amplified the target DNA in solution, and analyzed bands on an autoradiogram produced by gel electrophoresis of restriction enzyme digests of the target DNA bound to end-labeled radioactive probe molecules.

Accordingly, the invention aims to provide a system for automated gene identification of multiple samples, which prepares nucleic acids in the samples for testing, sufficiently amplifies target nucleic acid sequences and accurately detects their presence or absence in the samples.

Another object of the invention is to provide such a system which is adaptable to dispensing different quantities of different reagents.

Yet another object of the invention is to provide such a system wherein the reagents and solutions are forced through jet spray manifolds to evenly spray the matrices stacked in the reactor and diffuse through the matrices aided by gravity flow.

A further object of the invention is to provide such a system wherein airflow and heating regulate temperature and humidity.

A further object of the invention is to provide a system which can accommodate partial capacity loads, i.e., fewer matrices per run, or that can accommodate more than one probe per run.

A further object of the invention is to provide an automatic process and apparatus allowing identification of nucleic acid sequences that have been embedded or fractionated in a matrix whether or not prior extraction or purification of DNA has been performed in the invention.

A still further objective of the invention is to provide such a system wherein the temperature, time, pH, humidity, and pressure are monitored throughout the detection process.

Other objects and advantages of the invention will be more fully apparent from the ensuing disclosure and appended claims.

SUMMARY OF THE INVENTION

The process and invention in this patent utilizes the fundamental methodology from several state-of-the-art techniques to automate nucleic acid detection directly from biological material. The direct detection is automated by immobilizing the nucleic acids of each sample in a semi-solid matrix for DNA preparation, amplification and hybridization. In addition, the apparatus of the invention may be used to process gels of other known techniques in a new way and to automate these techniques or increase their sensitivity.

The automation of this invention makes direct detection available for innumerable clinical diagnoses and for environmental gene-tracking. Current practice for tracking microbes released into the environment is done by selecting marker genes on the same episome or genome as the engineered rDNA. The system of this invention provides direct, simultaneous monitoring of the rDNA from many samples without the time and expense required to cultivate the microbe. The frequency of the target sequence in the sample can be determined by measuring hybridization of the label to the single gene targets in situ. The target DNA in each sample is immobilized, exposed, amplified and located in a series of treatments to the matrix block in which the sample has been introduced.

Current practice detects viruses by indirect, immunological methods. The invention provides detection of viral sequences directly, regardless of the presence of circulating antibodies to viral antigens. It also enables analyses of environmental samples whereas immunological methods only work if the organisms are first isolated. The ability to detect single copies of a specific nucleic acid in biological or environmental samples makes this process revolutionary.

In the device of the invention, multiple matrices are housed in a reaction chamber through which reagents, solutions, enzymes and nucleotide primers and probes required for identification in this system are circulated. The matrices are stacked in horizontal planes and remain stationary while fluids and air are alternately moved around and through the matrices and the spaces between them. The liquid buffers and washes are sprayed into the reaction chamber, and gravity flow through the thin matrices and dehydration/rehydration of the matrices facilitate and control diffusion. This approach contrasts to the way that dried agarose gels or solid-support systems such as filters are agitated in hybridization solutions. The DNA present in the sample that has been introduced into an individual matrix remains anchored in the corresponding matrix and is separated from the other cellular particles or sample debris by lysing solutions and thorough washing. After washing, the sample is exposed to another solution to denature the DNA in situ. The denaturing solution is followed with a neutralizing treatment.

The gel matrices are dehydrated by the introduction of heated, moving air while the gel matrices remain stationary in the reaction chamber. The matrices are then rehydrated with the solution containing primer, nucleotide and polymerase molecules. The DNA is amplified by rounds of primer extension of target DNA. A short time is allowed for annealing of one or more primer pairs (a pair is defined as two primers that border opposite ends of a linear target DNA and are complementary to the opposite DNA strands) at an appropriate temperature. The temperature is changed to the optimal temperature for polymerase activity for a time period long enough to extend the DNA segment past the sequence to which its primer pair partner binds. The temperature is raised to a denaturation temperature for the DNA during a simultaneous partial dehydrating period. A new round is initiated by rehydrating with pulses of fluid to rehydrate the gel and the temperature is lowered to the annealing temperature. Each amplifying round theoretically increases logarithmically the copies of DNA target segments; the actual increase depends upon the efficiency of the polymerase. Approximately twenty to twenty-five rounds of amplification increase one DNA copy to two million copies, which is more than the number of copies needed for detection by current labeled probes. The number and choice of primer pairs and the number of replication cycles will vary according to the target nucleic acid. The sequence of a target nucleic acid must be known to determine a system to be used for detection. As more sequence information becomes available, the choice of primers for any one system may be changed to reflect a conserved genetic region and improve the specificity of detection. New technology may improve fidelity of primer annealing and DNA polymerization to allow accurate detection by incorporating labeled nucleotides in the amplification step, thus eliminating the need for a separate hybridization step in the detection process.

The gel matrices are dehydrated after the gene amplification reaches the level needed for detection by the hybridizing probe. The hybridizing probe consists of single-stranded DNA complementary to, but shorter than, the DNA target sequence and has one or more label molecules attached. The choice of nucleotide sequences for the hybridization probe reflects the same considerations stated for primer sequences.

The hybridizing solutions are pulse-sprayed into the reaction chamber. The shorter DNA probes diffuse and bind to the amplified copies within the matrices, but the diffusion conditions retard the leaching-out of the longer, amplified segments.

An alternate procedure involves primer pairs back to back along a target sequence in order to extend longer targets efficiently. The number of primer pairs in a linear or nested series may vary to accommodate the size-length of DNA required to immobilize the amplified segments during treatment. This alternative requires a ligase to incorporate each primer covalently to the linear molecule at its 5-prime end and the ligase needs to be thermo-resistant. In a particular system, such an enzyme would need to be isolated from nature, if it has not been already isolated.

Another alternate procedure involves adding the hybridization probes during the amplification phase. When single-stranded, labeled probe molecules are incorporated into the growing chains, they become part of the amplified DNA and sequential hybridization is not necessary. Since the process time is dramatically reduced in simultaneously amplifying and labeling the DNA, this step is desired. An enzyme for joining single strand nicks as described in the preceding paragraph is also necessary in order to insure the target sequence was labeled unambiguously over a background of randomly-primed, amplified DNA.

Each kind of labeled probe that hybridizes to the target DNA is detected according to the nature of its label molecule. The number of aggregates of detection signals corresponds to the number of original target sequences directly. In the case of higher density of targets or remelted agarose, the number can be interpolated.

For a fuller understanding of the nature and objects of the invention, reference should be made to the following detailed description, taken in connection with the accompanying drawing figures.

DETAILED DESCRIPTION OF THE INVENTION AND PREFERRED EMBODIMENTS THEREOF

The invention broadly comprises a system capable of fluid flow through the matrices and collection of fluids drained from the reactor before being either discarded or recycled. The system also includes a pump to maintain pressure in the jet-spray manifold during fluid flow. A system of valves controls selection of the treatments that will diffuse though the matrices and circulate through the system. The valves operate in the connections between the reactor chamber and the reservoirs which hold the reagents. A water line connects to the system through a valve and a regulator limits the maximum pressure. The pump is activated for auxiliary pressure if the water pressure reaches a designated lower limit. The system also includes blowers and heating elements to control the air or fluid temperature in the chamber.

In the invention, a detection system 1 for detecting nucleic acid targets broadly comprises a reaction chamber 2 (FIGS. 1-2) in which samples, individually embedded in matrices 3, are stacked horizontally in removable tray-racks 4 (FIG. 3) placed in the reaction chamber 2; a plurality of reservoirs 5 (FIGS. 1-2), each containing a solution or reagent for preparing the sample and promoting the detection of the target nucleic acid sequence; a pump 6 for transferring the solutions and reagents from the reservoirs 5 through secondary transfer lines 7, the supply manifold 8, and the main transfer line 9 to the jet spray manifolds 10 from which these fluids are sprayed into the reaction chamber 2; a system of swiches 11A-11E, 52 and 53 (and other switches not shown) and valves 12A-12K for regulating the flow of fluids; a drain system 13 for removing solutions and reagents from the reaction chamber 2; an air-flow system 14 that forces temperature-regulated air over the matrices 3 for drying and temperature control; a central microprocessor 15 which controls operation of the various components of the detection system 1; various sensors 16 and a power supply 17.

Figure 1:
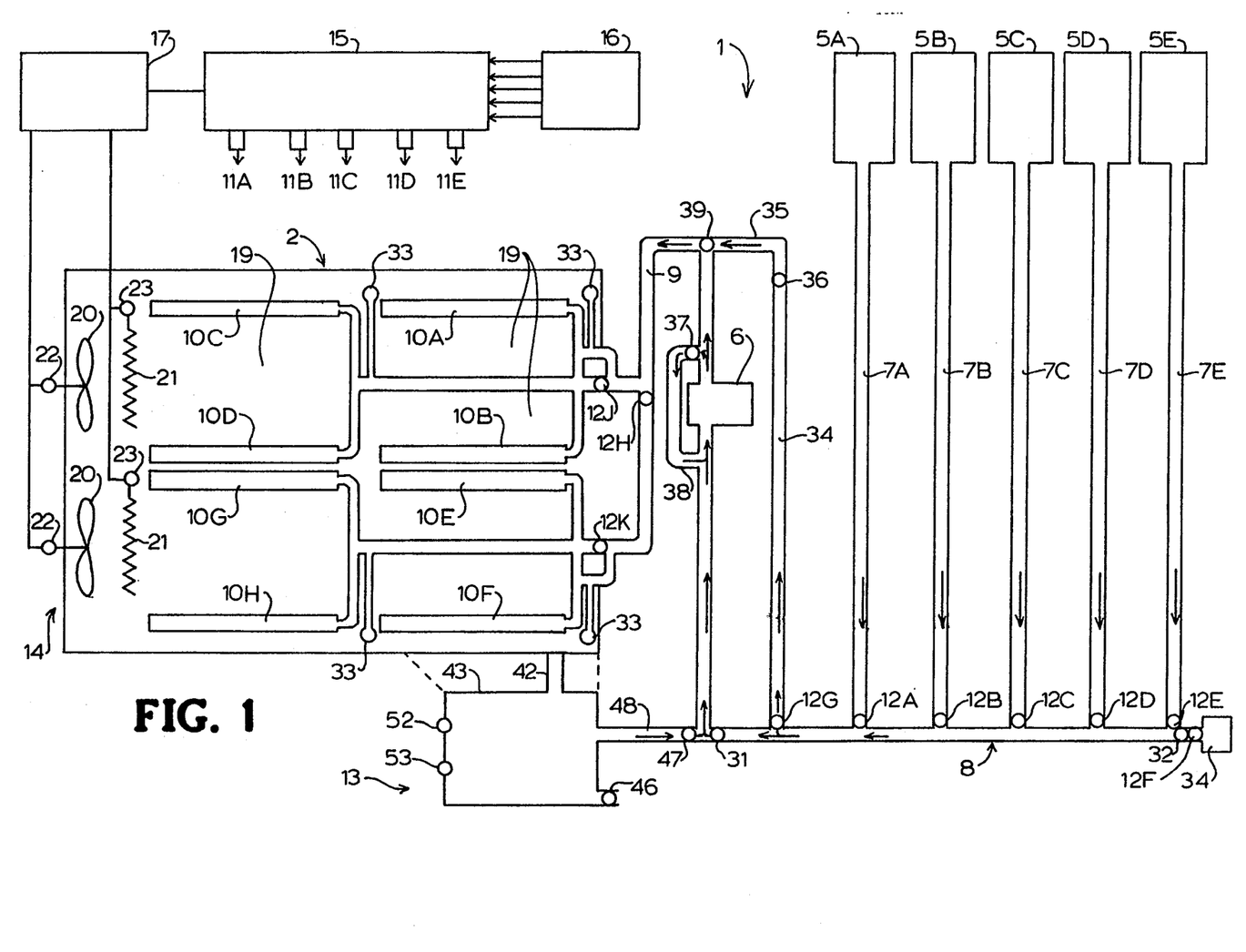
FIG. 1 is a schematic drawing of the automated gene identification apparatus of the invention.
Figure 2:
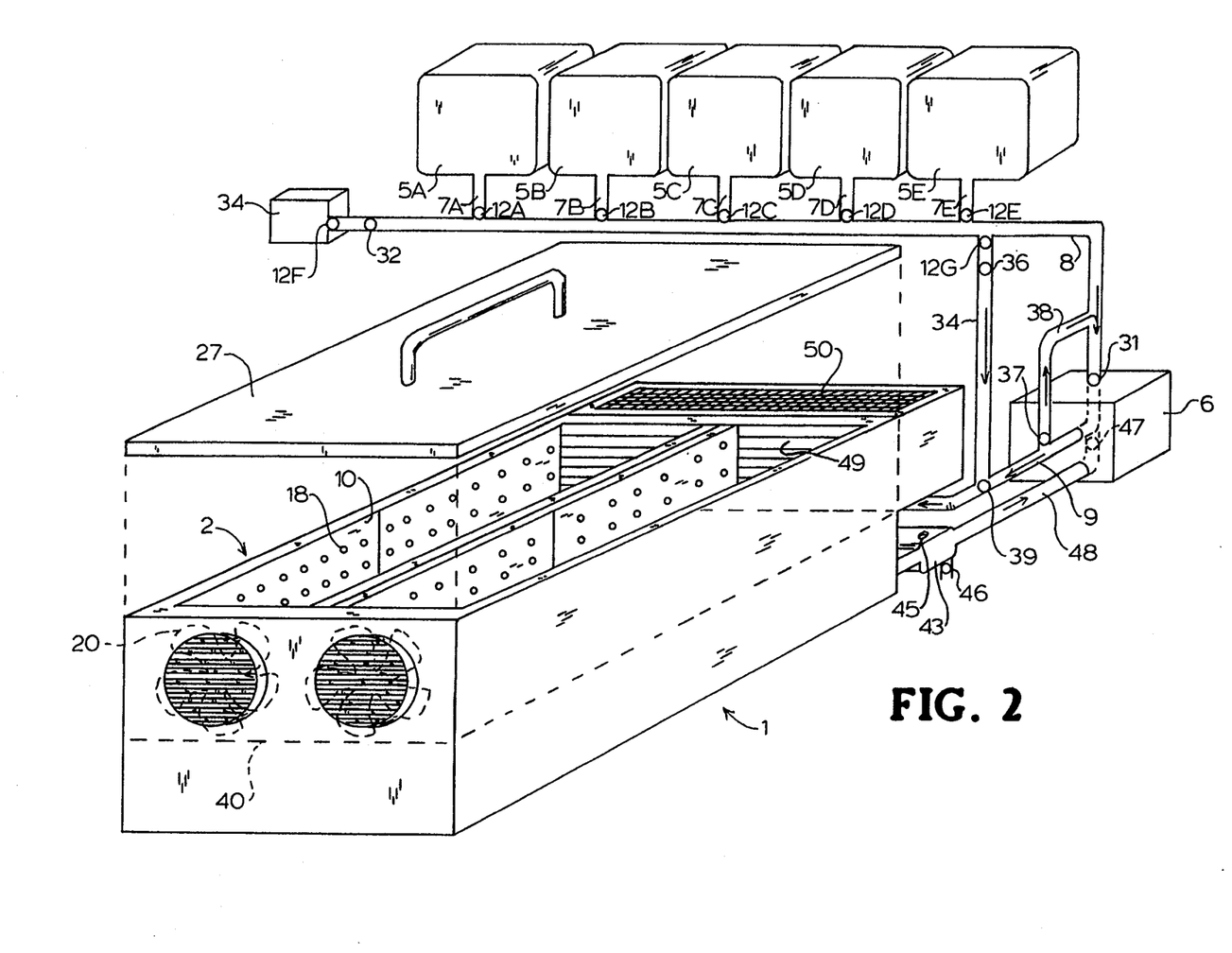
FIG. 2 is a perspective drawing of the overall gene identification apparatus embodying the invention.

The reaction chamber 2 consists of several jet-spray manifolds 10A-10H (FIG. 1). One side of each manifold 10, facing a tray-rack 4, has openings 18 through which liquids are sprayed over the matrices 3. The size, arrangement and number of openings 18 are designed to maximize a rapid, uniform flow of solutions over the upper surface of the matrices 3. The placement of manifolds 10 creates sections 19 in the reaction chamber 2 such that each section 19 holds one tray-rack 4. The number of sections 19 may be one or more, usually being four or more, and may be 10 or more. Four sections 19, each with two identical jetspray manifolds 10 located on opposite vertical sides and with two sets of fans 20 and heating elements 21 located on a third side of two sections 19, are shown in FIG. 2, but other arrangements may be used. The fans 20 and heating elements 21 on each side of the reaction chamber 2 have separate switches 22 and 23 in order to supply air-flow with or without heat to one or both sides of the reaction chamber 2.

The connections between the feed line 9 and the jet-spray manifolds 10 are shown in FIG. 1, according to the arrangement of manifolds illustrated in FIG. 2. Valves placed in these connections permit the system to accommodate partial loads, which means, if the number of samples loaded into the system 1 fills just one, two or three tray-racks 4, those sections with loaded tray-racks 4 may be sprayed in the system 1 with only the volume of solutions necessary for the manifolds 10 surrounding those sections 19. For example, valves 12H and 12J are closed if only one section 19 is to be used. Only valve 12H is closed if two sections 19 are to be used. Valves 12J and 12H are open and valve 12K is closed if three sections are used.

Figure 3:
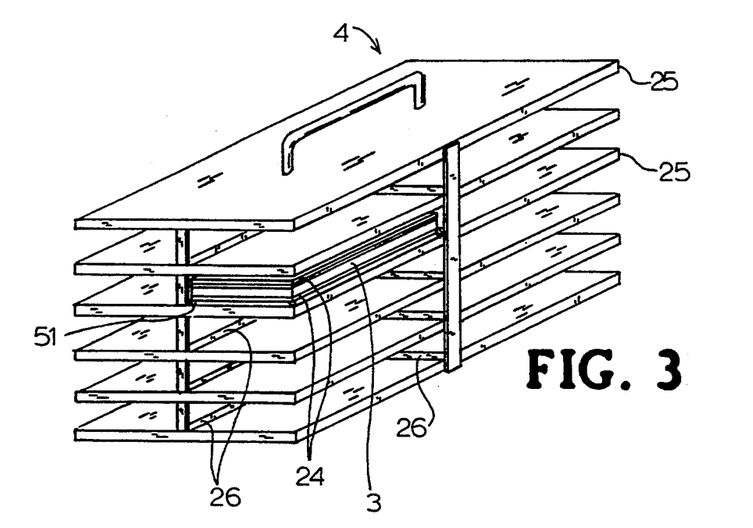
FIG. 3 is an exploded perspective view of a tray rack to hold the matrix and separators of FIG. 4.
Figure 4:
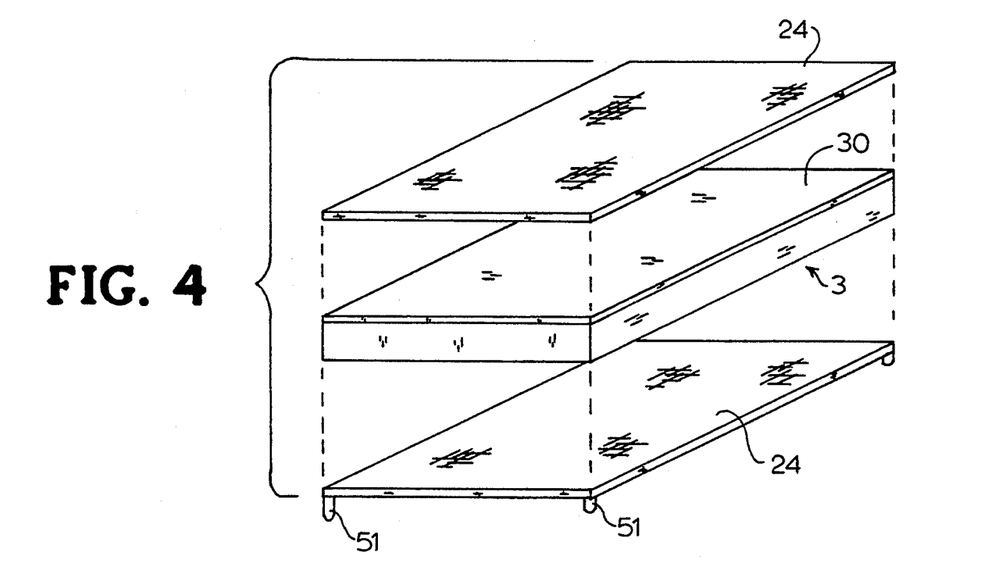
FIG. 4 is a perspective view of a matrix and separators that are placed on the tray rack shown in FIG. 3.
Figure 5:
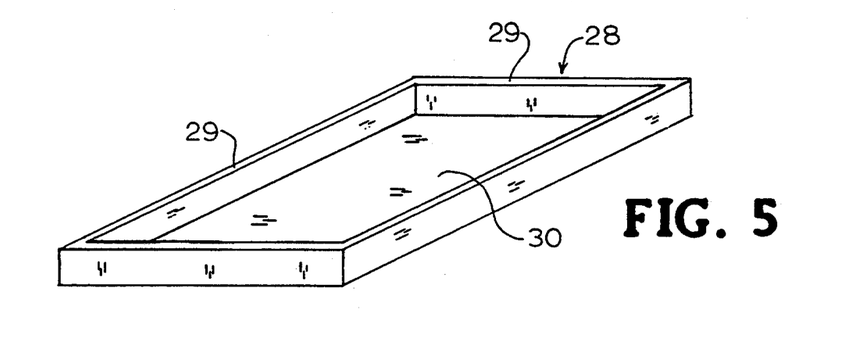
FIG. 5 is a view of a mold for forming a matrix into which a sample is placed for gene identification.

As shown in FIGS. 3-4, the matrices 3 are placed between rigid separators 24 so that each matrix 3 is suspended horizontally above a shelf 25 of the tray-rack 4. A preferred separator material is a polystyrene mesh that sandwiches the matrix so that the matrix does not touch the shelf 25 above or below the matrix. Each separator placed below a matrix preferably has small legs or knobs 51 on the separator to keep the separator 24 suspended above the shelf 25 upon which the separator is placed. The porous separator 24 and the space above and below the matrix allows free-flow of solutions or air around the matrix 3. The solid shelves 25 do not permit solutions or air from one matrix 3 to contact the matrices 3 in the other shelves 25 above or below it. Normally each tray-rack 4 has five covered shelves 25 and fits into a section 19 of the reaction chamber 2, but fewer or more shelves 25 may be used. The shelves 25 are sloped and equipped with drain slits 26 between the position of the matrices 3. Preferably the lengths of the knobs 51 on the bottom separator are adjusted with the knobs resting on the lower shelf area being longer than those resting on the higher, edge area of the shelves, so that the matrix itself does not slope. Tray-racks 4 are of at least three designs in order to accommodate matrices 3 of three different sizes. All three tray-rack designs have the same-sized shelves 25, but the drain slits 26 and slopes of the shelves 25 are arranged in such a way that each shelf 25 drains either four small-sized matrices 3, two medium-sized matrices 3 or one large matrix 3. The separators 24 are also designed to accommodate the three different matrix sizes. During operation of the system 1, the chamber cover 27 is placed on the reaction chamber 2.

A mold 28 for forming a gel is a frame with rigid sides 29 and a filter paper bottom 30 (FIG. 4). The mold is required to contain the sample and liquid matrix material (as discussed below) during solidification of the matrix material. After solidification of the matrix 3 containing the sample, the mold 28 (including the sample embedded in the matrix) is inverted and loaded between separators 24 onto a shelf 25 in the tray-rack 4. The paper layer 30 traps fluids and macromolecules so as to keep the upper surface of the underlying matrix more moist than the lower surface during liquid cycles and helps keep the matrix from curling during drying cycles. If the sample specimen has been fixed on a microscope slide, the slide may be overlaid with agarose or not and placed between separators in the tray racks. Gels subjected to prior electrophoresis may be placed with separators into tray racks.

The entire sequence of operation is controlled with a microprocessor or programmable controller 15 which serves both air and liquid processes. The liquid process begins with the processor energizing the appropriate valve 12 to open, and starting the pump 6 (FIGS. 1 and 2). Transfer of solutions and reagents from the reservoirs 5A–5E to the jet-spray manifolds 10 and into the reaction chamber 2 is accomplished by pump 6, which draws liquid into the manifold 8 from transfer lines 7A–7E and connects to the main transfer line 9. Pump valve 31 has its normal connection closed to pump 6 and closed along the supply manifold 8. During fluid flow, the pump valve 31 is actuated and the pump 6 draws liquids through the pump and pressurizes fluids in the main transfer line 9 and in the jet spray manifolds 10. If pressure as sensed by pressure switch 36 exceeds the desired limit, valve 37 opens to the pressure control bypass 38 enough to reduce the pressure by providing an escape route for the fluid from the fluid source being pumped. The fluids are dispersed as repeated fine sprays through small openings 18 in the manifold walls into the reaction chamber 2 where they saturate the matrices 3. The main transfer line feeds all manifolds in operation in such a way that an equivalent pressure enters each manifold and each of its openings. This may mean that the division of the main transfer line into the jet spray manifolds may occur centrally rather than on one side as shown in FIG. 1. The opening sizes vary to make equal spray to all matrices. They are large enough to prevent clogging and be easily cleaned, but small enough to create pressure in the jet spray manifolds when the pump is actuated. The pump maintains the desired pressure in the jetspray manifolds 10 for optimum saturation of the sample matrices 3.

The reservoirs 5A–5E are connected directly to corresponding secondary transfer lines 7A–7E. The secondary transfer lines 7A–7E are equipped with corresponding valves 12A–12E. These valves 12A–12E, in their normal or deactuated positions, close the reservoirs 5A–5E to the supply manifold 8. The valves 12A–12E are connected in parallel along the supply manifold 8. They are actuated independently by individual switches 11A–11E (FIG. 1). The connections between each switch 11A–11E and its respective valve 12A–12E are not shown. Although five reservoirs and five secondary transfer lines are shown, it is clear that fewer or more reservoirs may be used. Any of the transfer lines 7A–7E may be further equipped with the capability of injecting specific reagents into the solution passing through it.

The quantity of each solution or reagent transferred from reservoirs 5A–5E to the reaction chamber 2 is controlled by processor 15 activating the pump 6 for predetermined time periods or until the reservoir volume is depleted. The switches that control the valves 12A–12E in the transfer lines 7A–7E are actuated sequentially to provide a series of programmed treatments.

In the preferred embodiment, reservoir 5A contains a lysing and alkaline denaturing solution; reservoir 5B, a neutralizing solution; reservoir 5C, the reagents for amplification; reservoir 5D, the reagents for hybridization; and reservoir 5E, a hybridization wash solution. Thus, in a similar way, each treatment solution is sprayed over the matrices sequentially. A particular reservoir's contents can be changed for each detection system so that custom-made primers (for amplification) and labeled probes (for hybridization detection) can be made for any known target nucleic acid nucleotide sequence. If different tray-rack loads are being treated for different target sequences in the same operation, an optional system of mini-reservoirs 33 may be made available to add different primer probes to each manifold section. Drying cycles and water rinses are programmed between solution treatment sequences as necessary.

The outside water supply line 34 provides water rinses for the components occupying the reaction chamber 2 (matrices 3, tray-racks 4, separators 24), manifolds 8 and 10 and the main transfer line 9 between different treatment solutions or reagents. For this function, switches (not shown) actuate valves 12F and 12G to direct water flow through pump bypass loop 35. A pressure regulator 32 limits the maximum water line flow. The pump 6 and pump valve 31 are deactuated provided pressure switch 36 senses adequate water supply pressure. The pump 6 and pump valve 31 are actuated if the water supply pressure falls below the set minimum pressure needed to pressurize jet spray manifolds 10. Valve 39 prevents backflow to the pump during normal water rinsing or backflow to the pump bypass loop 35 when the pump is actuated.

Figure 6:
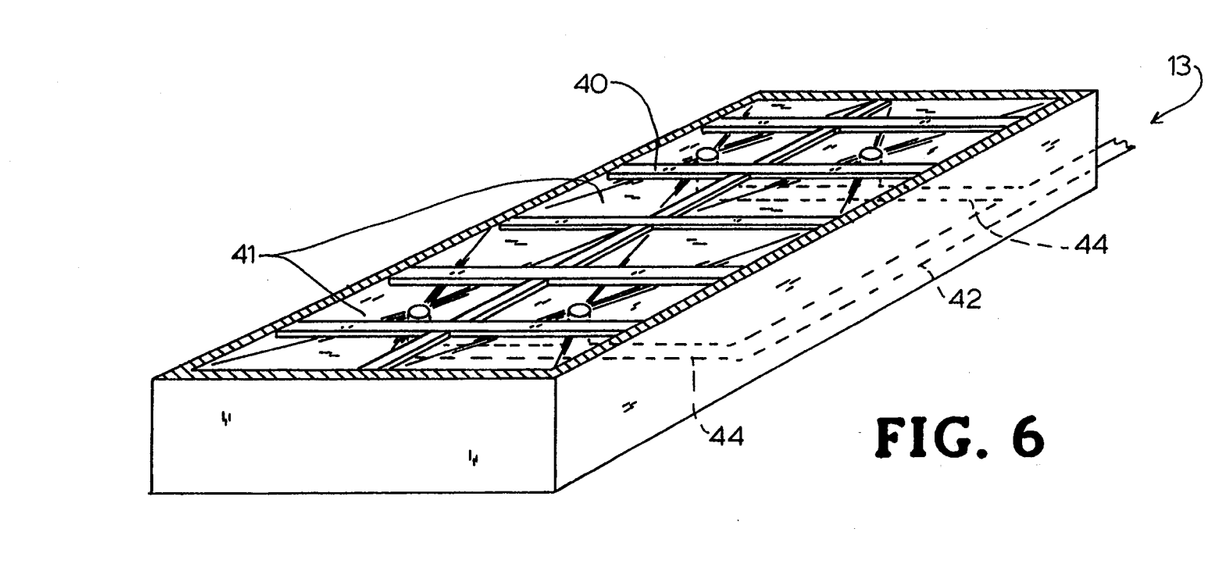
FIG. 6 is a perspective view of the drain system of the automated gene identification apparatus.

The drain system 13 (FIG. 6) consists of the drain slits 26 in the tray-racks 4, platform bars 40 that supports the tray-racks 4 in the reaction chamber 2, a drain floor 41 that slopes downward centrally within each section 19 to collecting lines 44 below the platform bars 40. Treatment solutions and water rinses in the reaction chamber 2 drain away from the matrices by gravity flow and drain from the slits 26 shown in FIG. 3 in the tray-racks 4 to the draining floor 41. Collecting lines 44 converge into a main drain line 42 where liquids then flow into the drain tank 43. An optional drain system (not shown) may be made available with the mini-reservoir 33 option in order to recycle different probes through different sections simultaneously. The drain tank 43 has a high-level volume switch 52 and a low-level volume switch 53. The drain tank 43 is further equipped with a vent 45 to permit rapid collection of liquids, a drain outlet valve 46 for discarding liquids and a valve 47 in the recycling line 48.

Two modes of operation allow fluids to be either discarded through the drain outlet 46 or recycled through the recycling line 48 to the reaction chamber 2. Normally both outlet valve 46 and valve 47 will be closed until high level switch 52, senses the desired volume. Then either outlet 46 or valve 47 will open depending on mode of operation. If the discard mode is programmed for a particular treatment phase, the drain outlet 46 is opened and the valve 47 to the recycling line 48 remains closed.

In the recycle mode, the valve to the drain outlet valve 46 remains closed and the valve 47 opens. Pump valve 31 and valve 47 may also be combined in one three-way valve. The recycling line 48 connects to the pump 6 and the main transfer line 9. The pump 6 remains activated or is activated and any actuated valves in the 12A-12E series are deactuated in the recycle mode in order to stop flow from the reservoirs. Liquid from the drain tank 43 is pumped through the recycling line 48, fills the main transfer line 9, and continues into the jet-spray manifolds 10. If the liquid level in the drain tank 43 falls below its desired level, the low-level switch 53 signals the microprocessor 15 to actuates a switch for the appropriate valve in the 12A-12E series in order to supply the make-up solution from a given reservoir to the reaction chamber 2 as needed until the high level switch 52 in the drain tank 43 again is activated. The high level switch 52 then stops the flow from the given reservoir 5 and recycling from the drain tank 43 continues as described.

The drying cycle serves to prepare the samples for enhanced uptake of subsequent solution treatments. A drying cycle is initiated by actuating fans 20 and heating elements 21 to force heated air horizontally through the shelves of the tray-racks 4 around the matrices 3. The air-flow assists evaporation of moisture around the matrices 3 and actual dehydration of the matrices. The side of the reaction chamber 2 opposite the blowers has vents 49 so air flows into a closed chamber. The air escape is covered by filters 50 to contain any airborne biological components released from the samples.

The switches for the fans and heating elements actuate and deactuate them separately to provide for different set temperatures in different phases of the dehydrating, amplifying or hybridizing cycles. Thermocouples (not shown) at strategic locations in the reaction chamber 2 sense a representative matrix temperature and transmit this signal to the microprocessor 15. As programmed, the microprocessor activates heating elements 21 as necessary to maintain the upper temperature at the desired setpoint for each stage of the molecular processing. The fans 20 can produce air flow when heating elements 21 are deactivated to lower matrix temperature quickly. Solutions in the liquid cycle, which are normally cooler than the maximum matrix temperature (for denaturation), may be sprayed over the matrices to accomplish quick lowering of temperature. The coordination of components in both the fluid and air-flow cycles provides the temperature control needed for the molecular processes in the detection system 1.

The system is also preferably equipped with pH and humidity sensors 16 to monitor reaction conditions. All parts of the detection system 1 that contact the solutions and reagents are made of chemically-resistant materials, such as teflon, glass or stainless steel so that all traces of nucleic acids may be cleaned from the apparatus surfaces between operations.

The process of the invention consists of the following stages: 1) matrix dispensing, sample mixing and DNA immobilization; 2) preparing DNA; 3) amplifying DNA target sequences; 4) hybridizing a labeled probe to the target; and 5) scanning the matrices for signal produced by bound label.

The uniqueness of this technology is the stabilization of nucleic acids in a matrix without extensive preparation of the biological sample, and the subsequent treatment of this matrix to prepare and identify the target genetic sequences automatically.

In the first stage of the invention, the dry matrix material is mixed with an aqueous buffer and kept liquid while sample is added, dispersed randomly throughout and poured into a mold. The preferred matrix material is agarose, a hydro colloid, because the procedures for amplifying and hybridizing DNA have been accomplished in agarose. The matrix is solidified by cooling it to a lower temperature or by chemical means to immobilize the sample in the matrix.

Any biological sample or environmental sample suspected of containing biological material is considered a sample. Each sample is mixed with aliquots of liquid matrix and allowed to solidify. A batch of sample matrices is subjected to subsequent treatments automatically in the reaction chamber 2. Blood, plasma, saliva, cerebrospinal fluid, lymph, urine, homogenous tissue, cell cultures, viruses, water, and soil are examples of sample material, but the process is not limited to these materials. For in situ identification of nucleic acids, tissue sections (prepared by standard methods for microscopy) may be overlaid with liquid matrix placed on tray rack shelves and then treated as other matrices. These matrices may also be scanned microscopically to localize the presence of target nucleic acids in the tissue. Gels containing nucleic acid samples, prepared by standard methods and size-fractionated by gel electrophoresis, may be amplified further and/or hybridized in this system.

The matrix allows entry and exit of reagents by diffusion to expose nucleic acids for identification by nucleic acid hybridization and/or antibody binding. A diffusion pressure is exerted on the gel matrix that maximizes molecular reaction kinetics. The matrix material allows diffusion yet maintains its integrity throughout the treatments that require nucleic acid immobilization. Drying steps during and between some treatments dehydrate the matrix blocks and the subsequent hydration with other liquid treatments enhances diffusion by creating a sponge-like uptake.

The binding of primers and probes requires prior melting of double-stranded DNA (dsDNA). This can be done by either a 95-degree C. temperature or an alkaline buffer. An alkaline buffer is used in the lysing procedure because it also inactivates biological activity as the DNA is cleansed of cellular constituents. A neutralizing treatment follows the lysing/alkaline denaturing stage. Alkaline conditions do not disturb the agarose matrix but do affect polymerase activity. The isolation and commercial availability of a polymerase that can withstand a brief 95-degree temperature has allowed temperature variation to be the means of denaturing dsDNA in cycles of PCR. The use of thermo-resistant polymerase for PCR in agarose is possible once the gels have been dried and then rehydrated. (A 95-degree C temperature does not compromise the integrity of a partially-dehydrated agarose matrix.)

The mold frames that hold the solid matrix vary in size according to the kind of sample being used. The preferred sizes are 50×75 mm for a small matrix, 100×75 mm for a medium-sized matrix, and 100×150 mm for a large matrix. The tray-rack are would be slightly larger than 100×150 mm to accomodate four small, two medium or one large matrix. The small and large sizes accomodate standard gel sizes for electrophoresis and allow hybridization analysis of restriction fragment length polymorphisms (RFLP's) in this system. The small size gel poured at a depth of 2.5 mm is for a sample volume of about 10 ml. A flat surface allows spatial enumeration of signal identification positions of target sequences during repetitive probing.

Assembly of the matrices is either manual or mechanically-assisted by an apparatus that automatically dispenses matrix aliquots, mixes the aliquot with a sample and pours the mixture into the molds. A sample dispenser, for example, can mix the heated matrix material in a liquid aliquot with each sample in a way that the sample is uniformly dispersed throughout the matrix and then poured into a mold. After poured matrices cool to room temperature and solidify, they are number-coded and inverted between separators and loaded in a tray-rack shelf. (Microscope slides with specimens would not be inverted.) Alternately, the samples and matrix material could be added to molds already positioned on tray-rack shelves.

In the second stage the tray-racks of matrices are treated as a unit for processing in the apparatus. If the nucleic acids are still in a biological specimen, the first solution is a detergent/enzymatic treatment to lyse cellular material and solubilize polypeptides and fatty molecules so they may be washed out of the matrix. Alkaline treatment, such as 0.5M NaOH is used to insure lysis and denature the immobilized DNA. Several volumes of wash buffer are diffused through the matrix to clear away biological molecules (except DNA, which is immobilized because of the nature of its structure) and also matrix contaminants (for example, sulfonated groups found in agarose) that might interfere with subsequent enzymatic activity. The wash solution also normalizes pH. The matrices are dehydrated by a drying cycle.

In the third stage the target sequences are amplified. The technology is provided by the PCR techniques. This amplification feature allows the subsequent identification of DNA amplified from one or more genetic sequences per biological. Polynucleotides, custom-designed primers and polymerase enzymes for DNA replication are added in the first solution to enter the dehydrated matrices. The matrices act like sponges to take up the solution. A polymerase chain reaction cycle consists of a) binding the primers, b) extending the DNA chain and c) denaturing the DNA molecules. Each step in the cycle requires a temperature change. Thus, typical temperatures at the three stages would be chosen from the following three ranges respectively, 37–40, 63–72 and 94–96 degrees C., but other temperatures may be useful for alternate procedures. The cycles repeat until sufficient target sequences are present for detection. The number of cycles necessary depends upon the efficiency of the polymerase and the detection sensitivity of the label being used.

In the fourth stage the hybridization of labeled DNA probe to the immobilized target DNA (RNA) is performed through a continuous cycling period of the probe solution for maximum binding kinetics. A typical procedure for hybridizing DNA with labeled oligonucleotide probes is presented in *Methods in Enzymology*, vol. 152, "Oligonucleotide probes for the screening of recombinant libraries," R. B. Wallace and C. G. Miyada, pages 432–442, 1987, Academic Press. Included are protocols for dried gel hybridizations. Prehybridization is not necessary. The dried gel is hybridized in a solution containing 5X SSPE, 0.1% SDS, 10 ug/ml sonicated, denatured *E. coli* or salmon sperm DNA and 1–10 ng/ml of labeled oligonucleotides. The gel is hybridized at $T_d$ minus 5 degrees or 60 degrees C., whichever is lower ($T_d$ is the temperature at which one-half of an oligonucleotide duplex becomes associated in 1M NaCl). Hybridization periods are 2 or more hours. The first washes with 6X SSC are at room temperature and then a stringent wash is done at the hybridization temperature minus 5 degrees C. for 1–3 minutes. The unbound probe DNA (RNA) is carefully washed from the matrix without disturbing DNA:DNA (DNA:RNA) hybrid complexes.

In the fifth stage the signal of the bound label is measured with a scanner appropriate for the label incorporated into the oligomer probe. Chemiluminescence, for example, may be detected by a photometer. The location and number of original target molecules present in the sample are reported by the signal. Scanner input data is entered into a microprocessor for matching the sample number with the identity of the sample and for further processing to determine the profile of the total sampled population. Software for the processor enables raw data of the sample to be structured with other information on the sample source and compared to a database.

The features and advantages of the present invention will be more clearly understood by reference to the following examples, which are not to be construed as limiting the invention.

EXAMPLE I

The following is an example of a reaction protocol using HIV-1 DNA sequences as a representative detection target, the sample tissue being human peripheral blood mononuclear cells:

(A) Mix a 5–9 ml sample of whole blood with 1–5 ml aliquots of matrix liquid, solidify and load them into the shelves of the tray rack. Load the tray rack into the main chamber.

(B) Connect the reservoirs filled with the proper reagents: reservoir 5A, lysing solution (0.5M NaOH, 0.1% SDS); reservoir 5B, neutralizing solution (50 mM KCl, 10 mM Tris; (2.5 mM MgCl$_2$, pH 8.4); reservoir 5C, primers at 1 uM each, nucleotides at 200 uM, polymerase at about 10 units per sample; reservoir 5D, labeled oligomer probes in hybridization solution based on the procedures referenced above (*Methods in Enzymology*); and reservoir 5E, hybridization wash solution.

(C) Select the proper program for this test and start the instrument's operation. Parameters such as the source of sample tissue and the number and length of target sequences affect the selection of the program.

(i) The microprocessor automatically controls the first two treatment solutions that strip proteins, dry the matrices and leave intact, denatured and neutralized DNA immobilized in the dehydrated matrix.

(ii) The dehydrated matrices are automatically rehydrated with the appropriate reagents for amplification of target sequences of DNA by primer extension in situ. This added solution contains oligomer primers (complementary to a conserved target gene), free nucleotides and polymerase molecules. Choice of primers and probes may change as critical functional domains of HIV proteins are determined and their corresponding conserved genetic sequences are identified.

(iii) Labeled oligomer probes are automatically hybridized to the amplified target DNA in situ and unbound probe is washed away.

(D) Remove the trays and quantitate the number of original target DNA copies present per sample.

The molecular processing is accomplished by processor-controlled commands for the fluid/air flow reactor system which serves the molecular manipulations by providing the necessary microenvironment in the individual matrices. The command system for controlling the microenvironment is chosen for specific gene probe sequences or different types of specimens and consists primarily of duration, pH and temperature of treatments containing standard and custom-made solutions. A user of the system needs only to enter the desired program of treatments into the processor, connect appropriate reservoir bottles to the system, add samples to matrix liquid, load the samples into trays and the trays into the chamber. The processor then automatically selects predetermined appropriate reaction conditions (time, duration, treatment solution, solvent or reagent) for the sample type, and initiates the appropriate commands, in the appropriate sequence, and at the appropriate times to obtain matrix conditions which allow the molecular manipulations.

In the preferred embodiment of the invention, the programing of the number and time intervals of treatments, the endpoints of each treatment, valve-control and electrical switching are computerized into the microprocessor. The system's flexible programming allows use of the device for research and clinical applications in which only one or two of the phases are required. Some examples of the different uses are preparation of large-sized DNA or intact chromosomes from cultured cells or organisms for other DNA manipulations, amplification of target DNA for other DNA manipulations, probe hybridization in gels in which nucleic acids have been size-fractionated by electrophoresis, or in situ amplification and hybridization of nucleic acids of tissue sections for microscopy. If the RNA in the sample is the target to be amplified, the sample is treated with reverse transcriptase to make a nucleic acid complement of the RNA just prior to the amplification step.

The scanning of the identification signal of the target sequence is incorporated into the final stage (D). The tray rack assembly enters a scanner and exposes the flat surface of each matrix to a scanner, which reads the signals. The scanning apparatus is interfaced with the microprocessor to give quantitative (location of signal) and qualitative (strength of signal) measurements. A representation of signal measurements made in situ may be printed out.

The ability to monitor specific nucleic acid sequences in biological material allows surveillance of genetic changes and fate-monitoring of known genetic changes. Both the lack of sensitivity of current probes and the labor-intensive preparation of the biological material has slowed application of recombinant DNA technology. The sensitivity of gene probes is increasing but some biological samples, especially those from the environment or a large population base, require massive sampling and screening to monitor the dispersal of the target gene. This method, which eliminates tedious sample preparation by automating the procedure, expands the ability to study gene competition, stability, dispersion and evaluate efficacy of new, recombinant DNA product treatments.

While the invention has been described with reference to specific embodiments thereof, it will be appreciated that numerous variations, modifications, and embodiments are possible, and accordingly, all such variations, modifications and embodiments are to be regarded as being within the spirit and scope of this invention.

I claim:

1. A method for studying genetic material of a sample in situ, comprising the steps of:
   (a) preparing a thin agarose matrix containing the sample in which the genetic material of the sample is anchored in separate positions in the matrix; and
   (b) treating the matrix with treatment liquids in an amount effective to remove interfering, non-genetic material from the sample; said treatment utilizing an apparatus comprising:
      (i) a reaction chamber for situating the samples;
      (ii) reservoirs for treatment liquids;
      (iii) treatment liquid transfer lines, said reservoirs connected to the reaction chamber by means of said treatment liquid transfer lines;
      (iv) means to control the addition to the reaction chamber of the treatment liquids in the reservoirs;
      (v) means to regulate air flow and temperature in the reaction chamber;
      (vi) a pump to cause the treatment liquids to move in the treatment liquid transfer lines; and
      (vii) means to remove treatment liquids from the reaction chamber;
   (c) amplifying target genetic material in the samples, wherein amplifying the genetic material consists essentially of utilizing repetitive enzymatic techniques selected from a group consisting of polymerase techniques to synthesize new DNA complementary to nucleic acid targets and ligase techniques to join together oligonucleotide sequences bound to their complementary nucleic acid targets when said oligonucleotide sequences bound to their nucleic acid targets are directly adjacent;
   (d) determining and enumerating the presence of nucleic acid targets;
wherein all sample treatment steps are done in a generally horizontal matrix.

2. A method for studying genetic material in a sample according to claim 1, wherein the sample is selected from a group consisting of cells and viruses and mixtures of cells and viruses, wherein nucleic acid targets are used to distinguish certain cells or viruses.

3. A method for studying genetic material in a sample according to claim 1, wherein the sample comprises tissue specimens, wherein nucleic acid targets are used to distinguish and enumerate certain cells in tissue from other cells.

4. A method for studying genetic material of a sample according to claim 1, wherein the matrix comprises an agarose gel prepared in such a way so that the matrix can be subjected to electrophoresis, and wherein the sample is subjected to electrophoresis in the agarose gel after step (c).

5. A method for studying genetic material in a sample according to claim 1, wherein a plurality of samples is placed in the apparatus and treated simultaneously, wherein each of said samples is individually embedded in a separate matrix section.

6. A method for studying genetic material of a sample according to claim 1, further comprising hybridizing a labeled nucleic acid probe to the genetic material.

7. A method for studying genetic material in a sample according to claim 1, wherein the matrix treatment steps comprise:
   (a) lysing the non-genetic material in the sample;
   (b) washing the matrix;
   (c) denaturing the genetic material;
   (d) neutralizing the genetic material
   (e) dehydrating the matrix; and the amplification step comprises:
   (f) rehydrating the matrix with solution containing nucleic acid amplification treatment liquids;
   (g) adjusting temperatures for amplification;
   (h) partially dehydrating the matrix during nucleic acid denaturation; and
   (i) repeating steps (f) through (h) until the nucleic acid is amplified sufficiently to be detectable by labeled probes.

8. A method for studying genetic material of a sample according to claim 1, wherein the matrix is prepared as a gel using a standard method for preparing gels for electrophoresis prior to step (a), and wherein the gel is treated with treatment liquids following electrophoresis of the genetic material in the gel.

9. A method for studying genetic material of a sample in situ, comprising the steps of:
   (a) fixing the sample containing the genetic material on a thin, flat support;
   (b) treating the sample with treatment liquids in an amount effective to remove interfering material from the genetic material of the sample;
   (c) amplifying the genetic material to be identified by synthesizing new DNA or RNA utilizing one or more of the following methods:
      (i) priming a specific sequence and extending synthesis with a polymerase, wherein said specific sequence is repeatedly used as a template;
      (ii) priming and extending synthesis of a specific sequence with two opposing primers and a polymerase to form primer extensions, wherein said specific sequence and the resulting primer extensions are repeatedly used as templates;
      (iii) binding oligonucleotide sequences to specific target sequences so that the oligonucleotide sequences are directly adjacent to each other and repeatedly ligating said adjacent oligonucleotide sequences; and
   (d) detecting said localized amplified genetic material by means selected from a group comprising the incorporation of labeled nucleotides and hybridizing labeled oligonucleotides to the amplified genetic material;
   wherein all the steps are done with the sample containing the genetic material to be identified fixed on said thin, flat support.

10. A method for studying genetic material in a sample according to claim 9, wherein the sample is selected from a group consisting of cells and viruses and mixtures of cells and viruses, wherein nucleic acid targets are used to distinguish and enumerate certain cells or viruses.

11. A method for studying genetic material in a sample according to claim 8, wherein the sample comprises tissue specimens, wherein nucleic acid targets are used to distinguish and enumerate certain cells in tissue from other cells.

12. A method for studying the genetic material of a sample according to claim 9 wherein at least one specific mRNA sequence contained in the genetic material of a biological specimen in situ is amplified, and said method further comprises firstly synthesizing cDNA within said specimen by repeated, primer extensions of a specific mRNA sequence in the presence of reverse transcriptase, and denaturing the cDNA:RNA hybrid molecules and polymerizing second strand DNA within said specimen by primer extensions on the cDNA templates in the presence of polymerase and primers that are complementary to the cDNA, wherein said method enables certain cells in the specimen containing said specific mRNA sequence to be enumerated and distinguished.

13. A method for studying genetic material in a sample wherein the sample comprises tissue sections in which treatment steps are done in a thin, flat, generally horizontal, format; comprising the steps of:
   (a) preparing the tissue sections on microscope slides by standard methods;
   (b) providing an apparatus for the treatments comprising:
      (i) a reaction chamber for situating the samples;
      (ii) reservoirs for treatment liquids;
      (iii) treatment liquid transfer lines, said reservoirs connected to the reaction chamber by means of said treatment liquid transfer lines;
      (iv) means to control the addition to the reaction chamber of the treatment liquids in the reservoirs;
      (v) means to regulate air flow and temperature in the reaction chamber;
      (vi) a pump to cause the treatment liquids to move in the treatment liquid transfer lines; and
      (vii) means to remove treatment liquids from the reaction chamber;
   (c) exposing and denaturing the nucleic acids in the samples;
   (d) repeatedly amplifying the genetic materials;
   (e) hybridizing a labeled nucleic acid probe to the gentic material; and
   (f) determining the presence of hybridized labled probe;
   wherein the steps (c) through (f) are performed on the microscope slides in said apparatus before microscopic analysis.

14. A method for studying genetic material in a sample in which the following treatment steps are done in a thin, flat, generally horizontal, agarose matrix; comprising the steps of:
   (a) preparing the sample in said matrix;
   (b) denaturing the nucleic acids in the samples;
   (c) repeatedly amplifying the genetic material to be identified;
   (d) hybridizing a labeled nucleic acid probe to the genetic material; and
   (e) determining the presence of hybridized labeled probe.

15. A method for studying genetic material in samples according to claim 14 wherein treatment steps a-e utilize an apparatus comprising:
   (a) a reaction chamber for situating the samples;
   (b) reservoirs for treatment liquids;
   (c) treatment liquid transfer lines, said reservoirs connected to the reaction chamber by means of said treatment liquid transfer lines;

(d) means to control the addition to the reaction chamber of the treatment liquids in the reservoirs;

(e) means to regulate air flow and temperature in the reaction chamber;

(f) a pump to cause the treatment liquids to move in the treatment liquid transfer lines; and (g) means to remove treatment liquids from the reaction chamber.

16. A method for studying genetic material of a sample in situ, comprising the steps of:

(a) preparing a thin, flat, semi-solid matrix containing the sample; said matrix comprising a material which is pourable as a liquid and is capable of immobilizing the sample when cooled to form a gel, said gel having a pore size which allows entry and exit of treatment liquids while fixing the positional orientation of nucleic acid targets within the sample;

(b) treating the matrix with treatment liquids in an amount effective to remove interfering, non-genetic material from the sample;

(c) repeatedly amplifying the genetic material to be identified in said matrix; and (d) utilizing the amplified genetic material for detection of specific genetic sequences.

* * * * *